United States Patent
Kobayashi

(10) Patent No.: US 6,297,186 B1
(45) Date of Patent: Oct. 2, 2001

(54) OSMIUM OXIDE COMPOSITION

(75) Inventor: Shu Kobayashi, 6-6-702, Sarugakucho 1-chome, Chiyoda-ku, Tokyo 101-0064 (JP)

(73) Assignees: Shu Kobayashi, Tokyo; Wako Pure Chemical Industries, Ltd., Osaka, both of (JP)

( * ) Notice: Subject to any disclaimer, the term of this patent is extended or adjusted under 35 U.S.C. 154(b) by 0 days.

(21) Appl. No.: 09/258,268

(22) Filed: Feb. 26, 1999

(30) Foreign Application Priority Data

Mar. 2, 1998 (JP) .................................................. 10-066207

(51) Int. Cl.$^7$ .............................. B01J 31/00; B01J 23/00; C08K 3/18; B32B 27/00; A61K 51/00
(52) U.S. Cl. .......................... 502/159; 502/325; 502/402; 502/406; 502/507; 524/431; 428/328; 428/319.3; 428/319.7; 428/319.9; 428/357; 428/402.2; 428/402.24; 428/403; 428/407; 424/1.29; 424/489; 987/18; 252/514
(58) Field of Search .................................... 502/159, 325, 502/402, 406, 507; 524/431; 428/328, 403, 407, 357, 402.2, 319.3, 319.7, 319.9, 402.24; 424/1.29, 489; 987/18; 252/514

(56) References Cited

U.S. PATENT DOCUMENTS

| | | | |
|---|---|---|---|
| Re. 29,419 | * 9/1977 | DeCraene | 204/290 F |
| Re. 35,692 | * 12/1997 | Debe | 427/154 |
| 3,947,277 | * 3/1976 | Carnahan et al. | 106/26 |
| 4,236,023 | * 11/1980 | Kesling, Jr. et al. | 560/207 |
| 4,824,969 | * 4/1989 | Austin et al. | 549/230 |
| 4,918,238 | * 4/1990 | Costantini et al. | 568/342 |
| 5,260,461 | 11/1993 | Hartung et al. | 549/447 |
| 5,302,257 | * 4/1994 | Gao et al. | 204/86 |
| 5,314,727 | * 5/1994 | McCormick et al. | 427/584 |
| 5,380,179 | * 1/1995 | Nishimura et al. | 419/36 |
| 5,391,533 | * 2/1995 | Peterson et al. | 502/262 |
| 5,419,817 | * 5/1995 | Gao et al. | 204/86 |
| 5,707,738 | * 1/1998 | Hou | 428/402 |
| 5,712,072 | * 1/1998 | Inaba et al. | 430/110 |
| 5,853,675 | * 12/1998 | Howorth | 422/179 |
| 5,882,723 | * 3/1999 | Tsou | 427/125 |
| 6,040,077 | * 3/2000 | Debe et al. | 429/40 |

FOREIGN PATENT DOCUMENTS

| | | |
|---|---|---|
| 2835 943 | 3/1980 | (DE) . |
| 3-081337 | 5/1991 | (JP) . |
| 4-505884 | 10/1992 | (JP) . |
| WO 91/00143 | 1/1991 | (WO) . |

OTHER PUBLICATIONS

Japanese Patent Abstract, Publication No. 03081337, Publication Date May 4, 1991.
Chem. Rev., 1994, "Catalytic Asymmetric Dihydroxylation", pp. 2483–2547.
Communications, 1989, "Catalytic Hydroxylation of Olefins by Polymer–Bound Osmium Tetroxide", pp. 45–47.
J. Org. Chem., 1998, "Microencapsulated Osmium Tetraoxide. A New Recoverable and Reusable Polymer–Supported Osmium Catalyst for Dihydroxylation of Olifins", pp. 6094–6095.
Tetrahedron Asymmetry, vol. 6, No. 11, "Polymeric Cinchona Alkaloids for the . . . ", pp. 2687–2694.
Tetrahedron Asymmetry, "Heterogeneous Catalytic Asymmetric Dihydroxylation of Olefins: a New Polymeric Support and a process Improvement", pp. 11321–11328.
Wolfgang A Herrmann et al; Journal of Molecular Catalysis A: Chemical 120 pp. 197–205, Oct. 1996.
Roy A. Johnson et al; Catalystic Asymmetric synthesis, VHC Publisher, New York, pp. 227–272, New York, 1993.
Carsten Bolm et al; Eur. J. Org. Chem., pp. 21–27, Aug. 1997.
Cainelli et al, Catalytic Hydroxlation of Olefins by Polymer–Bound Osmium Tetroxide, SYNTHESIS 1; No. 1, 1989, pp. 45–47. No month.
Choong et al, Polymeric Cinchona Alakloids for the Heterogeneous Catalytic Asymmetric Dihydroxylation of Olefins: The Influence of the Polymer Backbone Polarity on the Compatibility between Polymer Support and Reaction Medium; Tetrahedron: Asymmetry: vol. 6, No. 11, pp. 2687–2694, 1995. No month.
Pini et al., Heterogeneous Catalytic Asymmetric Dihydroxylation of Olefins: a new Polymeric Support and a Process Improvement; Tetrahedron; vol. 50, No. 38, 1994, pp11321–11328. No month.
Kolb et al., Catalytic Asymmetric Dihydroxylation; Chemical Rev.1994; vol. 94, No. 8; pp. 2483–2547, Jul. 1994.
Nagayama et al., Microencapsulated Osmium Tetaoxide. A New Recoverable and Reusable Polymer–Supported Osmium Catalyst for Dihydroxylation of Olefins; J. Org. Chem., 1998, vol. 63, pp. 1998.

* cited by examiner

*Primary Examiner*—Elizabeth Wood
*Assistant Examiner*—Patricia L. Hailey
(74) *Attorney, Agent, or Firm*—Armstrong, Westerman, Hattori, McLeland & Naughton, LLP

(57) ABSTRACT

The present invention provides an osmium oxide composition comprising an osmium oxide microencapsulated in an aromatic polyolefin (hereinafter abbreviated as MCOsO$_x$), a method for preparation of MCOsO$_x$, which comprises allowing an osmium oxide to contact with an aromatic polyolefin in an organic solvent, and precipitating MCOsO$_x$, an oxidizing agent comprising MCOsO$_x$, a method for preparing a chiral diol compound, which comprises reacting MCOsO$_x$, a chiral ligand and an olefin compound with each other, and a method for preparing a chiral diol compound, which comprises oxidizing an olefin compound with MCOsO$_x$ wherein a chiral ligand further coordinates to an osmium oxide.

9 Claims, No Drawings

OSMIUM OXIDE COMPOSITION

BACKGROUND OF THE INVENTION

The present invention relates to osmium oxide microencapsulated in an aromatic polyolefin and osmium oxidechial ligand complex microencapsulated in an aromatic polyolefin, which makes it possible to conduct an oxidation reaction of organic compounds in an enlarged industrial production scale.

It has been said that, among osmium oxide compounds, only oxides of tetravalent and octavalent osmium are actually existing in separated form, but additionally, oxides of divalent, trivalent and hexavalent osmium may be considered to exist. The oxides of octavalent osmium have been called osmium tetroxide or osmic acid when it is in an aqueous solution, and the oxides show a strong oxidation ability and thus they have been used as a special oxidizing agent and a catalyst in an organic synthesis. However, osmium tetroxide shows a melting point of 40.6 to 40.7° C., a boiling point of 131.2° C. and vapor pressure of 7 mm at 20° C. (or 52 mm at 55° C.), and has peculiar smell which can be perceived even in such an extraordinary low concentration as $2 \times 10^{-5}$ mg/ml, and further its vapor affects a mucosa of eye, among others, and is toxic to all respiratory organs.

Therefore, use of osmium tetroxide in an industrial scale has been troublesome, and it has been used only as an oxidizing agent for oxidizing a small amount of precious substances. Actually some technologies have been tried for the purpose of using this compound safely in an industrial scale. For instance, International Patent Publication (in Japanese) No. 505884/1992 provides a method for precipitating an osmium oxide on nitrogen-containing polymer from a solvent solution, and actually a product comprising about 1 wt % of osmium tetroxide immobilized on poly(4-vinylpyridine) (e.g. listed on a catalogue of Sigma-Aldrich) has been on the market.

However, in all of those known methods, all basic polymers containing nitrogen atoms, particularly cross-linked ones, have been used to utilize chemical binding effect between the osmium oxide and quaternary nitrogen atoms, and therefore their production has not been easy. Further, when those known compositions are used in actual reactions, the polymers immobilizing the osmilm oxide are gradually decomposed under oxng conditions (Journal of Molecular Catalysis A: Chemical, vol. 120 (1997) p 203 right column), and therefore the problems upon handling have not yet been solved, and reuse of the compositions is still restricted.

Further, in the product disclosed in the above International Patent Publication (in Japanese) No. 505884/1992, as stated therein, the osmium oxide immobilized on polymer containing nitrogen atoms does not exist in the form of osmium tetroxide but in the form of osmium trioxide or, sometimes, oxide of a polymer or in a reduced form such as oxoanion, and thus it cannot be said that the osmnium oxide is immobilized on the polymer as the stable form of osmium tetroxide and consequently the effect as an oxidizing agent of the product is apparently poor as compared with that of osmium tetroxide.

Recently, it is reported that oxidation of olefin compounds by using osmium oxide to which a chiral ligand is attached can give the corresponding chiral products ("Catalytic asymmetric synthesis, VHC Publisher, New York, 1993, P.227–272," or "Chem. Rev., 94, 2483–2547 (1994)," etc.). But in those asymmetric oxidations, an osmium oxide itself is used without, for instance, nnmobilized on polymers, etc., and therefore, the recovery and reuse of the osmium oxide is usually difficult.

On the other hand, it is reported that an asymmetric oxidation is conducted using a complex of an osmium tetroxide and a polymer on which a chiral ligand is immobilized ("Eur. J. Org. Chem., 1998, 21–27" etc). However, in this method, introducing of the chiral ligand in the polymer is not so easy and further the polymer containing the chiral ligand thus obtained has to be farther reacted with osmium tetroxide. Additionally, the osmium tetroxide in the complex comes off from the complex little by little during the asymmetric oxidation, and therefore reuse of the complex many times is substantially impossible.

SUMMARY OF TIHE INVENTION

The present inventors have extensively made study m order to solve such problems as mentioned above to realize the improvement, on the basis of which the present invention has been accomplished.

Namely, the present invention provides an osmium oxide composition comprising an osmium oxide microencapsulated m an aromatic polyolefin (hereinafter abbreviated as $MCOsO_x$).

Further, the present invention provides $MCOsO_x$ wherein a chiral ligand further coordinates to an osmium oxide (hereinafter abbreviated as $MCOsO_x$-chiral ligand complex).

Still further, the present invention provides a method for preparation of $MCOsO_x$, which comprises allowing an osmium oxide to contact with an aromatic polyolefin in an organic solvent, and precipitating $MCOsO_x$.

Furthermore, the present invention provides a method for preparing $MCOsO_x$-chiral ligand complex, which comprises allowing $MCOsO_x$ to contact with a chiral ligand.

Still furthermore, the present invention provides a method for preparing $MCOsO_x$-chiral ligand complex, which comprises allowing an osmium oxide, a chiral ligand and an aromatic polyolefin to contact with one another in an organic solvent, and precipitating an osmium oxide-chiral ligand complex microencapsulated in the aromatic polyolefin ($MCOsO_x$-chiral ligand complex).

Additionally, the present invention provides an oxidizing agent comprising $MCOsO_x$.

Still additionally, the present invention provides an oxidizing agent comprising $MCOsO_x$-chiral ligand complex.

Still further additionally, the present invention provides a method for preparing a chiral diol compound, which comprises oxidizing an olefin compound with $MCOsO_x$-chiral ligand complex.

Stil furthermore additionally, the present invention provides a method for preparing a chiral diol compound, which comprises reacting $MCOsO_x$, a chiral ligand and an olefin compound with each other.

DETAILED DESCRIMION OF THE PREEERRD EMBODIMENTS

As the osmium oxide of the present invention, use is generally made of osmium tetroxide, but other osmium oxides such as osmium dioxide can be used. The osmium oxide may be commercially available one.

A part of osmium in $MCOsO_x$ of the present invention is partly reduced by a small quantity of non-reacted unsaturated bonds usually existed in the aromatic polyolefin, and such partly reduced osmium oxide as above is also included in the osmium oxide of the present invention.

The aromatic polyolefin of the present invention (hereinafter sometimes abbreviated as the polymer of the present invention) includes homopolymers and copolymers which are prepared by polymerization of aromatic olefins, such as, styrene, α-substituted styrene or their ring-substituted derivatives. The substituent in the ring-substituted derivatives of styrene or α-substituted styrene may be any one which does not give bad influence on conducting the microencapsulating of osmium oxide by the method of the present invention and does not reduce the effect of the osmium oxide in $MCOsO_x$ as an oxidizing agent or a catalyst, and includes an alkyl group such as a methyl group, an ethyl group and an isopropyl group, an alkoxy group such as a methoxy group, an ethoxy group and an isopropoxy group, etc.

The monomer unit other than styrene or α-substituted styrene type unit in the copolymers is not specifically limited and may be any one which does not give bad influence upon conducting the microencapsulating of osmium oxide by the method of the present invention and does not reduce the effect of the osmium oxide in $MCOsO_x$ as an oxidizing agent or a catalyst, and includes ethylenically unsaturated catboxylic acids such as acrylic acid, methacrylic acid, maleic acid and fumaric acid, ethylenically unsaturated carboxylic acid esters such as methyl acrylate, methyl methacrylate, butyl methacrylate and dimethyl maleate, ethylenically unsaturated amide or imide compounds such as acrylamide, methacrylamide and maleimide, vinyl esters such as vinyl formate and vinyl acetate and cyano-con aining ethyleically unsaturated compounds such as aclyronirile and methacrylonitrile.

The copolymers of the present invention also includes those prepared by using a divalent unsaturated monomer such as butadiene and divinylbenzene together with the aromatic olefin such as styrene, α-substituted styrene and their ring-substituted derivatives, if necessary, further together with a monomer other than the styrene, α-substituted styrene and their ringsubstituted derivative type of copolymers are acrylonitrile-butadiene-stylene Tesin (ABS-resin) and styrene-divinylbenzene copolymer.

A basic nitrogen-containing monomer is not desirable as the monomer other than styrene and α-methyl styrene, but there may be used only when its amount is such one as giving no considerable influence.

In the polymer of the present invention, when the molecular weight of the aromatic polyolefin to be used is too low, a mechanical strength of the resulting $MCOsO_x$ or $MCOsO_x$-chiral ligand complex becomes low, and when it is too high, the preparation of $MCOsO_x$ or MCOsOi-chiral ligand complex requires much work and time.

A weight-average molecular weight of the polymers of the present invention is generally 1,000 to 5,000,000, preferably 200,000 to 350,000, and a degree of polymerization of the polymer is 10 to 50,000, preferably 2,000 to 3,500.

As the polymers of the present invention, use may be made of those produced after a conventional method or commercially available ones.

The preparation of $MCOsO_x$ of the present invention is conducted after a so-called microencapsulating technology for relatively large molecular weight substances, which has been used in medical and foodstuff fields, such as one disclosed in Pharmaceutica Acta Helvetiae vol.53 (1978) p 17–23 and p 33–39 as the general discussion.

Namely, the osmium oxide is allowed to contact with the aromatic polyolefin, for instance, by mixing the both, in an organic solvent until the resulting mixture becomes homogeneous and then precipitating the resultant to recover a solid part, for instance, by filtration.

More particularly, for instance, the polymer of the present invention as mentioned above is dissolved in a suitable organic solvent under heating with stirring. An osmium oxide such as osmium tetroxide in an amount of 0.02 to 0.4 wt part, preferably 0.1 to 0.2 wt part, relative to 1 wt part of the polymer is added to the above obtained solution, followed by stirring at 25 to 50° C. until the resulting mixture becomes homogeneous. Termination of the treatment can be confirmed by this homogeneity. The resulting homogeneous solution is ice-cooled with stirring. When precipitating out of a solid is observed, a poor solvent to the polymer used is added so as to complete the precipitating out. Recovering the precipitated product by filtration gives $MCOsO_x$ of the present invention. It is voluntary that the obtained product is further washed and dried after a conventional manner.

The organic solvent to be used in the preparation as mentioned above is not specifically limited so long as it can dissolve the polymer of the present invention, and includes aromatic hydrocarbons such as benzene, toluene and xylene, ketones such as methyl ethyl ketone, ethers such as diethyl ether and tetrahydrofuran, esters such as ethyl acetate, halogenated hydrocarbons such as chloroform, dichloroethane and carbon tetrachloride, saturated cyclic hydrocarbons such as cyclohexane, etc. Preferable solvent is variable because it depends upon the kind of the polymer to be used, and when polystyrene is used, for instance, cyclohexane, dichloroethane, etc. is preferable because it has a suitable solubility to polystyrene. When ABS-resin is used, for instance, tetrahydrofuran is preferable because it has a suitable solubility to ABS-resin.

The poor solvent to the polymer to be used in the preparation as mentioned above somewhat depends upon the kind of the polymer, and includes lower alcohols such as methanol and ethanol, aliphatic hydrocarbons such as n-hexane and petroleum ether, etc., among which methanol is preferable from industrial point of view.

$MCOsO_x$-chiral ligand complex of the present invention is prepared, for example, by a method mentioned below.

Namely, for instance, $MCOsO_x$ and a chiral ligand in an amount of 0.001 to 10 mol %, preferably 0.1 to 1 mol %, relative to 1 mol % of the osmium oxide in $MCOsO_x$ are added to a suitable solvent, followed by stirring at 0 to 50° C., preferably 15 to 40° C. for a few minutes to a few ten minutes. Recovering the precipitation by filtration gives $MCOsO_x$-chiral ligand complex of the present invention. It is voluntary that the obtained product is further washed and dried after a conventional manner The solvent to be used in the preparation method mentioned above is not specifically limited so long as it cannot dissolve $MCOsO_x$ of the present invention under the condition for conducting an object reaction and give any bad influence on an object reaction, and includes water, acetonitrile, dimethylformamide, dimethyl sulfoxide, ketones such as acetone and methyl ethyl ketone, lower alcohols such as methanol, ethanol and isopropanol, ethers such as diethyl ether, 1,4dioxane and tetrahydrofuran, esters such as ethyl acetate, hydrocarbons such as benzene, toluene, xylene and cyclohexane, halogenated hydrocarbons such as chloroform, dichloroethane and carbon tetrachloride, etc.

These solvents may be used alone or in a suitable combination of two or more thereof In case of the combination of two or more thereof there is exemplified by a mixed solvent of water, acetonitrile and acetone as a preferable combination of these solvents.

MCOsO$_x$-chiral ligand complex of the present invention is also prepared by allowing an osmium oxide, a chiral ligand and the polymer of the present invention to contact with one motion in a suitable organic solvent after the above-mentioned manner for the production of MCOsO$_x$.

More particularly, for instance, the polymer of the present invention as mentioned above is dissolved in a suitable organic solvent under heating with string. An osmium oxide such as osmium tetroxide in an amount of 0.02 to 0.4 wt part, preferably 0.1 to 0.2 wt part, relative to 1 wt part of the polymer and a chiral ligand in an amount of 0.001 to 10 mol %, preferably 0.1 to 1 mol %, relative to 1 mol % of the osmium oxide are added to the above obtained solution, followed by stirring at 25 to 500° C. until the resultant becomes homogeneous. Termination of the treatment on can be confirmed by this homogeneity. The resulting homogeneous solution is ice-cooled with stirring. When precipitating out of a solid is observed, a poor solvent to the polymer used is added so as to complete the precipitating out. Recovering the precipitated product by filtration gives MCOsO$_x$-chiral ligand complex of the present invention. It is voluntary that the obtained product is further washed and dried after a conventional manner.

The chiral ligand used in the present invention includes compounds having the following properties;

a) having optical activity
b) including generally one or more, preferably two or more ligands which have a lone pair, and
c) having a bulky structure.

The chiral ligands having the above properties are particularly preferable in a case of using them together with MCOsO$_x$ in asymmetric oxidization reaction.

The ligand having a lone pair mentioned above is one derived from oxidizing accelerator, including tertiary amine compounds such as pyridine compounds (i.e. pyridine, a substituted pyridine derivative, etc.), quinuclidine compounds (i.e. quinuclidine, a substituted quinuclidine derivative, etc.), an N-substituted piperidine derivative and phthalazine.

The bulky structure mentioned above is, for instance, a cyclic structure, which may be any of a monocyclic structure or a polycyclic structure, and includes one derived from aliphatic cyclic hydrocarbon rings such as a cyclopentane ring and a cyclohexane ring, aromatic rings such as a benzene ring, a naphthalene ring and an anthracene ring, aliphatic heterocyclic rings such as a pyrrolidine ring, a piperidine ring and a quinuclidine ring, aromatic heterocyclic rings such as a pyridine ring, a pyrazine ring, a pyrimidine ring, a pyridazine ring, a indole ring, a isoquinoline ring, a quinoline ring, a phthalazine ring and a pyrazino[2, 3-d]pyridazine ring, and their ring-substituted derivatives, whose substituent has no bad influence upon the object reaction.

The substituent includes alkyl groups of 1 to 6 carbon atoms such as a methyl group, an ethyl group, an n-propyl group, an isopropyl group, a cyclopropyl group, an n-butyl group, an isobutyl group, a sec-butyl group, a tert-butyl group, an n-pentyl group, an isopentyl group, a neopentyl group, a tert-pentyl group, a 3,3-dimethylbutyl group, a 1,1imethylbutyl group, a 1-methylpentyl group, a cyclopentyl group, an n-hexyl group, an isohexyl group and a cyclohexyl group, alkoxy groups of 1 to 6 carbon atoms such as a methoxy group, an ethoxy group, an n-propoxy group, an isopropoxy group, a cyclopropoxy group, an n-butoxy group, an isobutoxy group, a sec-butoxy group, a tert-pentyloxy group, a 3,3dimethylbutoxy group, a 1,1-dimethylbutoxy group, a 1-methylpentyloxy group, a cyclopentyloxy group, an n-hexyloxy group, an isohexyloxy group and a cyclohexyloxy group, halogen atoms such as a chlorine atom, a bromine atom, a fluorine atom and a iodine atom, a thiol group, an amino group and a phenoxy group which may have a substituent such as alkyl groups of 1 to 6 carbon atoms.

Among the chiral ligands having the above properties, more preferable examples include ones which can catalyze the general asymmetric oxidation reaction using an osmium oxide such as osmium tetroxide. The specific examples of the ligands are as below, which may have substituents having no bad influence upon the reaction.

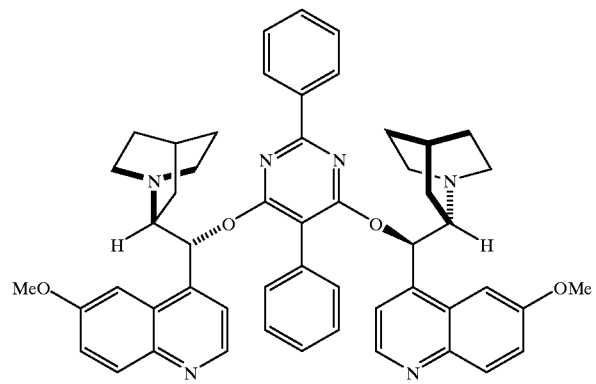

-continued
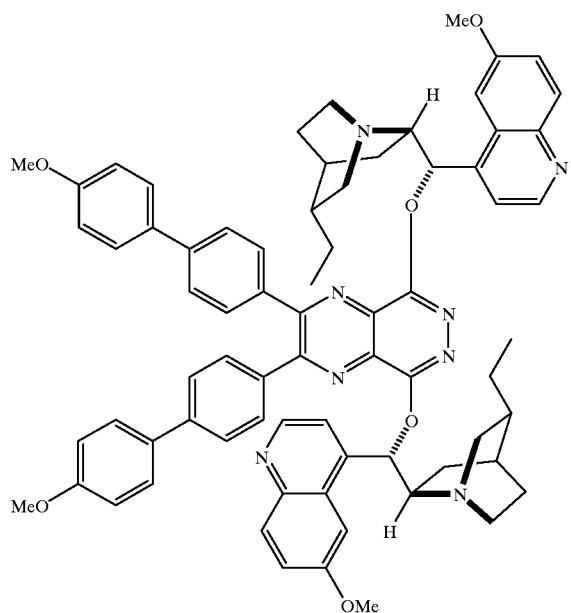
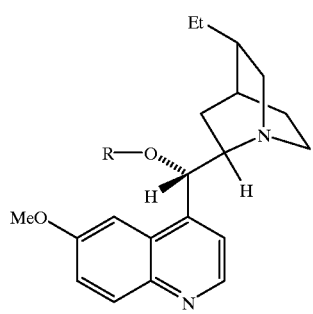
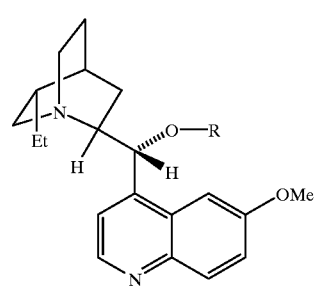
R = H        (DHQD)         R = H        (DHQ)
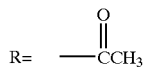 (DHQD-OAc)   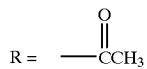 (DHQ-OAc)
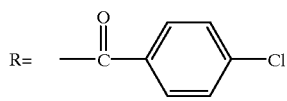 (DHQD-CLB)   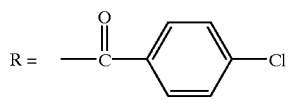 (DHQ-CLB)
R = 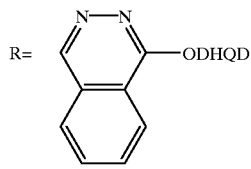 [(DHQD)$_2$-PHAL]   R = 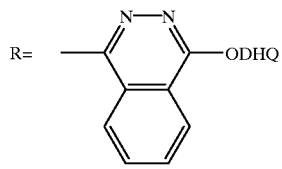 [(DHQ)$_2$-PHAL]
R = 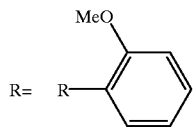   R = 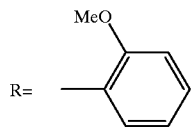
R = 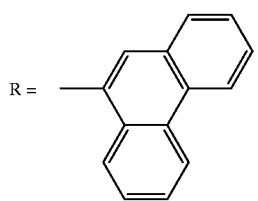 (DHQD-PHN)   R = 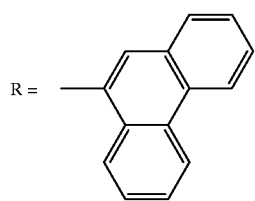 (DHQ-PHN)

-continued
R = 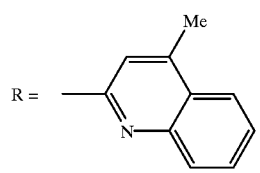 (DHQD-MEQ)
R = 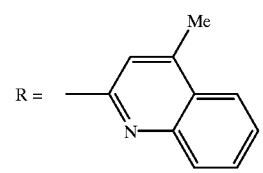 (DHQ-MEQ)
R = 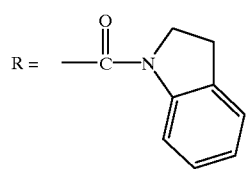 (DHQD-IND)
R = 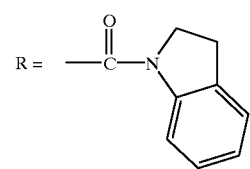 (DHQ-IND)
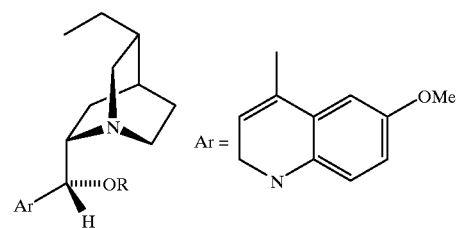
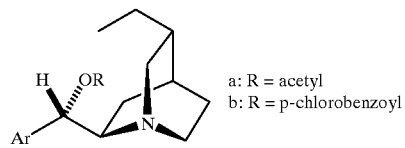
a: R = acetyl
b: R = p-chlorobenzoyl
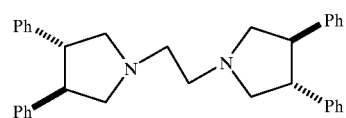
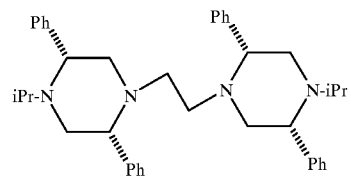
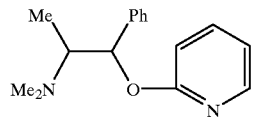
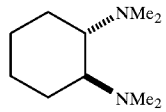
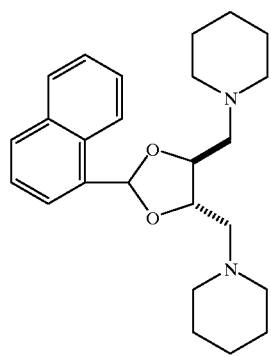

-continued

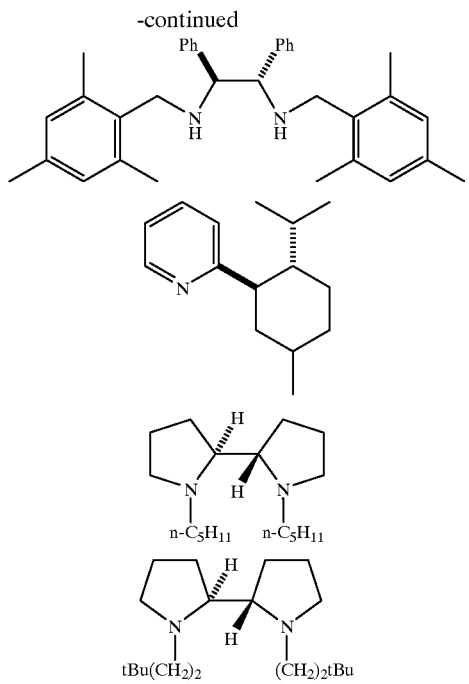

The organic solvent to be used in the preparation method mentioned above is not specifically limited so long as it can dissolve the polymer of the present invention, and includes aromatic hydrocarbons such as benzene, toluene and xylene, ketones such as methyl ethyl ketone, ethers such as diethyl ether, 1,4dioxane and tetrahydrofuran, esters such as ethyl acetate, halogenated hydrocarbons such as chloroform, dichloroethane and carbon tetrachloride, saturated cyclic hydrocarbons such as cyclohexane, etc. Preferable solvent is variable because it depends upon the kind of the polymer to be used, and when polystyrene is used, for instance, cyclohexane, dichloroethane, etc. are preferable because they have a suitable solubility to polystyrene. When ABS-resin is used, for instance, tetrahydrofuran is preferable, because it has a suitable solubility to ABS-resin.

These solvents may be used alone or in a suitable combination of two or more thereof.

The poor solvent to the polymer to be used in the preparation as mentioned above somewhat depends upon the kind of the polymer, and includes lower alcohols such as methanol and ethanol, aliphatic hydrocarbons such as n-hexane and petroleum ether, etc., among which methanol is preferable from industrial point of view.

In thus obtained $MCOsO_x$ or $MCOsO_x$-chiral ligand complex of the present invention, the osmium oxide is contained, presumably in microencapsulated state in the polymer of the present invention, and is considered to be maintained in the microcapsule formed by the polymer of the present invention by electronic interaction between the aromatic ring of the polymer and a vacant orbit of the osmium.

The resulting product comprises fine particles having an average particle size of 100 to 200 μm.

The characteristics of the product are as follows;
1. an osmium oxide is in microencapsulated state and thus can safely be handled,
2. no smell peculiar to an osmium oxide is perceived any longer even when it is kept standing under usual atmosphere,
3. the product shows such high storage stability that it can maintain its activity even after 12 months storage, while the activity of conventional products is reduced after 6 months storage even under tightly sealed conditions (Synthesis, p46, 1989 right column), and
4. after the product is used as an oxidizing agent, it can be recovered quantitatively and thus recovered product can be reused repeatedly. For instance, even after reusing the product ten times or more, almost no reduction of the catalytic activity of the product is observed.

These characteristics suggest that the osmium oxide is coated or covered by the polymer as a matrix, and that whole structure does not collapse during storage or even after using as an oxidizing agent, while its activity, for instance, as an oxidizing agent, can be maintained, and further these characteristics support such presumption on a concrete structure of the product that each of fine particles of the osmium oxide is microencapsulated or included in the polymer as a matrix but the microencapsulation or inclusion in this case is not complete so that the microencapsulated or included particles have fine holes or pores which directly connect to atmosphere(see Pharmaceutica Acta Helvetiae vol.53 (1978) p 17–23 and p 33–39). In other words, it is presumed that the osmium oxide microencapsulated or included in the polymer as a matrix is not completely shielded to atmosphere.

In $MCOsO_x$ or $MCOsO_x$-chiral ligand complex of the present invention, it is possible to contain an osmium oxide in an amount of 10% or more, at maximum about 20%, while conventional products contain it only in about 1% at most, and also in this respect, the present composition is remarkably excellent as compared with conventional products.

$MCOsO_x$ or $MCOsO_x$-chiral ligand complex of the present invention can be formulated into various forms depending upon the kind of the poor solvent used and conditions for adding the osmium oxide to the polymer, and even when it is formulated into a bulk form, the product can be put into practical use after pulverizing upon necessity.

$MCOsO_x$ or $MCOsO_x$-chiral ligand complex of the present invention can be used as an oxidizing agent in oxidizing reactions of organic compounds, quite similarly to osmium tetroxide itself. The use for this purpose may follow conventional ones in oxidizing reactions of organic compounds by osmium tetroxide, and the total amount of $MCOsO_x$ or $MCOsO_x$-chiral ligand complex to be used can be determined on the basis of the osmium oxide content in $MCOsO_x$ or $MCOsO_x$-chiral ligand complex so that an osmium oxide can exist in the reaction system in an amount necessary to the reaction.

When $MCOsO_x$ or $MCOsO_x$-chiral ligand complex of the present invention is used as an oxidizing agent, other conventional oxidizing agent can be co-used therewith. Other oxidizing agent co-usable may be any one which has been used in oxidizing reactions of organic compounds with the use of osmium tetroxide, and includes hydrogen peroxide, potassium ferricyanide, potassium periodate, sodium periodate, organic peroxides such as t-butyl hydroxyperoxide, N-oxide compound such as 4 methylmolpholine N-oxide and trimethylamine N-oxide.

In addition, the above-mentioned oxidation reaction using $MCOsO_x$ and a chiral ligand, or using $MCOsO_x$-chiral ligand complex of the present invention includes asymmetric oxidation reaction. In these oxidation reactions, stereoselective oxidation of olefin compounds having a chiral carbon atom, diastercoselective oxidation of olefin compounds having a chiral protective groups, and enantiomeric asymmetric oxidation are included and $MCOsO_x$ of the present invention with a chiral ligand, or $MCOsO_x$-chiral ligand complex of the present invention is able to use in all of these asymmetric oxidations.

For instance, a chiral diol compound is obtained at high optical yield by subjecting an olefin compound to an asymmetric oxidation reaction using $MCOsO_x$ and a chiral ligand, or using $MCOsO_x$-chiral ligand complex.

Preparation method for a chiral diol compound of the present invention can be conducted by a method mentioned below.

Namely, for instance, $MCOsO_x$ and a chiral ligand in an amount of 0.001 to 10 mol %, preferably 0.1 to 1 mol %, relative to 1 mol % of the osmium oxide in $MCOsO_x$ are added to a suitable solvent, and an olefin compound in an amount of 1 to 100,000 mol %, preferably 1 to 100 mol %, relative to 1 mol % of the osmium oxide in $MCOsO_x$ is dropwisely added to the resulting solution, if necessary, in the presence of other suitable oxidizing agent, generally at 0 to 80° C., preferably at 15 to 40° C., generally for 5 to 50 hours, preferably for 20 to 30 hours, whereby the object asymmetric oxidation reaction takes place. After the reaction, $MCOsO_x$-chiral ligand complex is removed by filtration and the filtrate is subjected to a conventional suitable after-treatment, whereby the objective chiral diol compound can easily be obtained at high optical yield.

Also, such an asymmetric oxidation reaction can be conducted by reacting an olefin compound with MCOsOi-chiral ligand complex, which is previously prepared.

Namely, the chiral diol compound can be obtained by either of the above two methods.

However, the former method in which a preparation of $MCOsO_x$-chiral ligand complex and an asymmetric oxidation of an olefin are conducted in so-called one-pot reaction is preferable, for the reason that it needs less amount of a chiral ligand for the asymmetric oxidation reaction than the latter.

The olefin compound to be used in the method of preparing a chiral diol compound mentioned above is not specifically limited so long as it has generally one or more, preferably one or two polymerizable double bond in its molecule, and includes an aliphatic olefin, an aromatic olefin, etc.

The solvent to be used in the method mentioned above is not specifically limited so long as it does not dissolve $MCOsO_x$ or $MCOsO_x$-chiral ligand complex of the present invention under the condition for conducting an object reaction and give any bad influence on an object reaction, and according to properties of $MCOsO_x$ or $MCOsO_x$-chiral ligand complex and an olefin compound to be used, use is made of water, acetonitrile, dimethylformamide, dimethyl sulfoxide, ketones such as acetone and methyl ethyl ketone, lower alcohols such as methanol, ethanol and isopropanol, ethers such as diethyl ether, 1,4dioxane and tetrahydrofuran esters such as ethyl acetate, hydrocarbons such as benzene, toluene, xylene and cyclohexane, halogenated hydrocarbons such as chloroform, dichloroethane and carbon tetrachloride, etc.

These solvents may be used alone or in a suitable combination of two or more thereof. In case of the combination of two or more thereof, there is exemplified by a mixed solvent of water, acetonitrile and acetone as a preferable combination of these solvent.

$MCOsO_x$-chiral ligand complex used in the above mentioned reaction can be recovered quantitatively and thus recovered $MCOsO_x$-chiral ligand complex can be reused repeatedly for an asymmetric oxidation reaction.

In order to increase an optical yield of a chiral diol compound, it is desired to co-use an additional chiral ligand in the case of reusing $MCOsO_x$-chiral ligand complex three times or more.

Further, in order to increase oxidation activity of $MCOsO_x$, it is desired to co-use other oxidizing agent mentioned above.

In the following, the present invention is further explained referring to Examples, but the present invention is not limited thereto by any means.

EXAMPLE

Example 1

Preparation of $MCOsO_x$ (Using polystyrene)

Five grams of polystyrene (molecular weight 280,000) was dissolved in 100 ml of cyclohexane with stirring at 50 to 60° C. and then 1 g of osmium tetroxide was added to the mixture, followed by stirring for about 1 hour until the mixture becomes homogeneous. The resulting mixture was cooled to 25° C. and then further ice-cooled. When polystyrene started to solidify, about 150 ml of methanol was added to the mixture. After standing for 8 hours, the precipitates were recovered by filtration, washed with methanol and dried under vacuum to give 5.7 g of $MCOsO_x$ microencapsulating 700 mg of osmium oxide (hereinafter abbreviated as PS-$MCOsO_x$).

Example 2

Preparation of $MCOsO_x$ (in case of Using ABS-resin)

Ten grams of ABS-resin was added in 200 ml of tetrahydronfuran (THF) and the mixture was heated at 70 to 80° C. with stiring. And then 2 g of osmium tetroxide was added to the ABS-resin of THF solution, followed by stirring for about 1 hour until the mixture becomes homogeneous. The resulting mixture was cooled to 25° C. and then further ice-cooked. When the resin started to solidify, about 300 ml of n-hexane was added to the mixture. After standing for 8 hours, the precipitates were recovered by filtration, washed with methanol and dried under vacuum to give 11.9g of MCOsO$_x$ microencapsulating 1.9 g of osmium oxide (hereinafter abbreviated as ABS-MCOsO$_x$).

Example 3

Preparation of ABS-MCOsO$_x$ Having a Chiral Ligand

The mixture of ABS-MCOsO$_x$ (0.5 mmol as OsO$_4$), obtained by example 2, and hydroquinidine 1,4-phthalazinediyl diether ((DHQD)$_2$PHAL) as a chiral ligand (1 mmol) were added to a mixture of water-acetonitrile-acetone (1:1:1, by vol.) (35 ml) with stirring by 10 minutes, and the precipitate was isolated by filtration, washed with methanol and dried to give a complex of ABS-MCOsO$_x$ and (DHQD)$_2$PHAL (hereinafter abbreviated as ABS-MCOsO$_x$-(DHQD)$_2$PHAL).

Example 4

An Oxidizing Reaction by PS-MCOsO$_x$ 2.5 Millimole of 3 β-cholesterol was dissolved in 50 ml of diethyl ether, and MCOsO$_x$ containing osmium tetroxide in an amount equivalent to 2.5 mmol was added thereto, followed by stiring at 25° C. for 30 hours to cause a reaction to take place. MCOsO$_x$ was removed from the reaction solution, and a crude keto compound was recovered from the filtrate and purified by silica gel column chromatography (eluent: benzene) to give 3-cholestanol at a yield of 90%.

Example 5

An Oxidizing Reaction by PS-MCOsO$_x$ Together with N-oxide

Fifty mmol of cyclohexene, 5 mole % of PS-MCOsO$_x$ and 1.3 equivalent of N-methylmorpholine N-oxide (NMO) were stirring in mixed solvents comprising 15 ml of water, 15 ml of acetone and 15 ml of acetonitrile under argon streams at 25° C. for 24 hours to allow a reaction to take place. Then about 150 ml of methanol was added to the resultant to terminate the reaction and PS-MCOsO$_x$ was removed by filtration. The filtrate was concentrated under reduced pressure and the resulting crude product was purified by silica gel column chromatography to give 1,2-cyclohexane diol at a yield of 84%.

Sinularly to the above, analogous reactions were further conducted using ten kinds of olefin compound as substrate to give the result as shown in Table 1. In Table 1, a case of using cyclohexene as an olefin compound was also shown. The PS-MCOsO$_x$ recovered was able to reuse after washing with methanol.

TABLE 1

| Olefin | Reaction temperature | Reaction time | Yield (%) |
|---|---|---|---|
| Cyclohexene | 25° C. | 24 hrs. | 84 |
| Cyclooctene | 25° C. | 38 hrs. | 81 |
| 1-Decene | 25° C. | 24 hrs. | 68 |
| 3-Hexene | 25° C. | 48 hrs. | 74 |
| 1-Hexene | 25° C. | 24 hrs. | 89 |
| vinylcyclohexane | 25° C. | 24 hrs. | 83 |
| methylenecyclohexane | 25° C. | 24 hrs. | 84 |
| 2-methyl-1-pentene | 25° C. | 24 hrs. | 78 |
| 1-methylcyclohexene | 25° C. | 24 hrs. | 76 |
| 3-methyl-2-butene | 25° C. | 24 hrs. | 63 |
| 2-methyl-2-heptene | 60° C. | 24 hrs. | 83 |

Example 6

Recovery and Reuse of PS-MCOsO$_x$

The process in the above Example 5 was repeatedly conducted using PS-MCOsO$_x$ recovered and change in the oxidizing effect as an oxidizing agent was studied. Consequently, such a good result as below was obtained. Namely, the yield of 1,2-cyclohexane diol after the 8$^{th}$ run was 85%, while those before the 8run were 83 to 85%, and the recovery rate of PS-MCOsO$_x$ was almost quantitative.

Example 7

Asymmetric Oxidation with ABS-MCOsO$_x$ Having a Chiral Ligand

NMO (1.43 mmoo) was added to a slurry of ABS-MCOsO$_x$ (0.5mmol as OsO$_4$) and (DHQD)$_2$PHAL (1 mmol) in water-acetonitnle-acetone (1:1:1, vol.) (3.5 ml), and then trans-β-methylstyrene (1.1 mnmol) was dropped to the slurry at 25° C. for 24 hours. The ABS-MCOsO$_x$-(DHQD)$_2$PHAL was filtered off and washed with MeOH. A mixture of the filtrate and the washing solvent was concentrated under reduced pressure, and the resulting residue was purified by silica gel column chromatography to obtain a diol compound represented by formula [1] mentioned below at a yield of 95%. The optical yield of the diol compound was 85%ee. Since osmium was not detected in the filtrate, osmium tetroxide did not leak out from the ABS-MCOsO$_x$-(DHQD)$_2$PHAL.

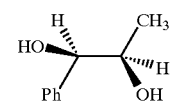

[1]

Example 8

Asymmetric Oxidation with PS-MCOsO$_x$ Having a Chiral Ligand

Trans-β-methylstyrene was oxidized with PS-MCOsO$_x$ (0.5 mmol as OsO$_4$) instead of ABS-MCOsO$_x$ after the asymmetric oxidation of example 7 to give a diol compound at a yield of 80%. The optical yield of the diol compound was 56%ee.

Example 9

Recovery and Reuse of ABS-MCOsO$_x$ Having a Chiral Ligand in Asymmetric Oxidation The process in the Example 7 was repeatedly conducted using recovered ABS-MCOsO$_x$-(DHQD)$_2$PHAL for the study of changing in the oxidizing ability of ABS-MCOsO$_x$-(DHQD)$_2$PHAL as an oxidizing agent. Consequently, the object diol compound was obtained at a yield of 99%, and the optical yield of the diol compound was 86%ee.

As mentioned above, the osmium oxide composition comprising an osmium oxide microencapsulated in the aromatic polyolefin of the present invention can more easily be prepared as compared with osmium oxides immobilized on a basic nitrogen-containing polymer, and though the product contains high concentration of osmium oxide, it can safely be handled under normal conditions, and further it is excellent in its reactivity. Therefore, it can be utilized in oxidizing reactions of organic compounds quite similarly to osmium tetroxide, and it can quantitatively be recovered and can be reused. Further in case of oxidizing reaction of an olefin compound using it together with a chiral ligand, a chiral diol compound can be obtained at high optical yield. Because of those characteristics, the composition of the present invention is such a valuable one as being able to be utilized easily and at high efficacy in an industrial scale.

What is claimed is:

1. An osmium oxide composition comprising an osmium oxide microencapsulated in an aromatic polyolefin matrix to form a composition of porous particles having fine pores that directly connect to the atmosphere.

2. The osmium oxide composition according to claim 1, wherein the osmium oxide is osmium tetroxide.

3. The osmium oxide composition according to claim 1, wherein the aromatic polyolefin is a homopolymer or a copolymer of styrene, α-substituted styrene or their ring-substituted derivative.

4. The osmium oxide composition according to claim 1, wherein the aromatic polyolefin is polystyrene or acrylonitrile-butadiene-styrene resin.

5. An osmium oxide composition according to claim 1, wherein the composition is fine particles having an average particle size of 100 to 200 $\mu$m.

6. An osmium oxide composition according to claim 1, wherein an amount of the osmium oxide contained in the composition is 10 to 20 wt %.

7. An osmium oxide composition according to claim 1, wherein the osmium oxide composition is prepared by allowing the osmium oxide to contact with an aromatic polyolefin in an organic solvent, and precipitating the osmium oxide microencapsulated in the aromatic polyolefin.

8. An osmium oxide composition according to claim 1, wherein the osmium oxide composition is prepared by mixing osmium oxide with an aromatic polyolefin in an organic solvent until the resulting mixture becomes homogeneous and precipitating the resultant to recover a solid part.

9. An osmium oxide composition comprising an osmium oxide microencapsulated in an aromatic polyolefin wherein a chiral ligand further coordinates to the osmium oxide.

\* \* \* \* \*